(12) United States Patent
McLaughlin

(10) Patent No.: US 11,553,887 B2
(45) Date of Patent: Jan. 17, 2023

(54) LIMITED DATA PERSISTENCE IN A MEDICAL IMAGING WORKFLOW

(71) Applicant: Shenzhen Mindray Bio-Medical Electronics Co., Ltd., Shenzhen (CN)

(72) Inventor: Glen W. McLaughlin, San Carlos, CA (US)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 226 days.

(21) Appl. No.: 16/809,859

(22) Filed: Mar. 5, 2020

(65) Prior Publication Data
US 2021/0275121 A1 Sep. 9, 2021

(51) Int. Cl.
| G16H 30/00 | (2018.01) |
| A61B 6/00 | (2006.01) |
| A61B 6/03 | (2006.01) |
| G16H 40/63 | (2018.01) |
| G16H 30/40 | (2018.01) |
| G16H 30/20 | (2018.01) |

(52) U.S. Cl.
CPC .............. *A61B 6/468* (2013.01); *A61B 6/032* (2013.01); *A61B 6/037* (2013.01); *A61B 6/5205* (2013.01); *G16H 30/20* (2018.01); *G16H 30/40* (2018.01); *G16H 40/63* (2018.01)

(58) Field of Classification Search
None
See application file for complete search history.

(56) References Cited

U.S. PATENT DOCUMENTS

| 5,734,915 A * | 3/1998 | Roewer | G06F 3/04845 715/202 |
| 6,173,068 B1 * | 1/2001 | Prokoski | A61B 5/7264 382/125 |
| 6,569,097 B1 * | 5/2003 | McMorrow | G06Q 40/08 600/437 |
| 9,888,143 B1 * | 2/2018 | Janakiraman | G06F 3/0652 |
| 2001/0051881 A1 * | 12/2001 | Filler | G16H 40/67 705/3 |
| 2002/0016718 A1 * | 2/2002 | Rothschild | G16H 30/20 705/2 |
| 2003/0163031 A1 * | 8/2003 | Madden | G16H 70/60 600/300 |
| 2009/0054768 A1 * | 2/2009 | Halmann | A61B 8/00 600/437 |

(Continued)

*Primary Examiner* — John A Pauls
(74) *Attorney, Agent, or Firm* — Kory D. Christensen

(57) ABSTRACT

A medical imaging system comprises an operator terminal configured to obtain at least one image of a patient generated by a medical imaging device, receive one or more notes pertaining to the at least one image from an operator of the medical imaging device, store a clean set of images including the at least one image in at least one server, annotate the at least one image with the one or more notes to generate a set of annotated images; tag the set of annotated images as non-persistent, and store the set of annotated images in the at least one server; wherein the at least one server is configured to provide to a physician terminal both the clean set of images and the annotated set of images stored for the patient and automatically delete the one or more images tagged as non-persistent after review thereof by the physician.

16 Claims, 5 Drawing Sheets

(56) References Cited

U.S. PATENT DOCUMENTS

2011/0123075 A1\* 5/2011 Nie .......................... G06T 7/12
                                                                        382/128
2016/0357918 A1\* 12/2016 Tochilnik .............. G06F 16/116
2017/0290569 A1\* 10/2017 Utsunomiya .......... A61B 8/464

\* cited by examiner

LIMITED DATA PERSISTENCE IN A MEDICAL IMAGING WORKFLOW

TECHNICAL FIELD

This disclosure relates to medical imaging and, in particular, to limited data persistence in a medical imaging workflow.

BACKGROUND

Research into medical imaging workflow efficiency has focused on improving the throughput of a medical imaging device, such as an ultrasound imaging device, but has not considered the entire workflow from the moment a patient arrives to the point at which a diagnosis is made and submitted. Currently, after scanning the patient, the operator (sonographer) typically needs to leave the room and wait for the reviewing physician to become available, and, at that time, use their handwritten notes and findings along with their memory to transfer knowledge to the physician while the collected images are reviewed. This wastes time that the sonographer could use in preparing the exam room for the next patient, as well as the additional time required for the physician to listen to comments by the sonographer and relate them to the image sequence.

SUMMARY

According to one aspect, a medical imaging system includes an operator terminal, which obtains images of a patient generated by a medical imaging device, such as an ultrasound imaging device, an X-ray imaging device, a computed tomography (CT) imaging device, a magnetic resonance imaging (MRI) device, or a positron-emission tomography (PET) imaging device.

The operator terminal may also receive one or more notes pertaining to the images from an operator of the medical imaging device. The notes may exclude standard measurements, calculations, and identifications of anatomical structures being imaged by the medical imaging device. Instead, the notes may reflect observations or findings of the operator of the medical imaging device. In one embodiment, the operator terminal stores a clean set of images in at least one server, such as a Digital Imaging and Communications in Medicine (DICOM) server.

In addition, the operator terminal may annotate the images with the notes provided by the operator in order to generate a set of annotated images. In one embodiment, the annotated images are tagged as non-persistent, either automatically or based on an operator selection, and stored in the server. For example, the images may be tagged with a custom DICOM tag.

The operator terminal may also receive one or more photographs related to the patient from the operator of the medical imaging device. The photographs may be tagged as non-persistent and stored in the server. The photographs may be generated by a secondary imaging modality other than the medical imaging device, such as a mobile device (e.g., tablet, cell phone) with a digital camera.

Additionally, the operator terminal may receive one or more audio recordings of the operator of the medical imaging device pertaining to the images. The audio recordings may be may be tagged as non-persistent and stored in the server. Moreover, the operator terminal may further receive one or more additional notes from the operator of the medical imaging device pertaining to the images. The additional notes may be may be tagged as non-persistent and stored in the server.

In one embodiment, the server provides to a physician terminal both the clean set of images and the annotated set of images stored for the patient, allowing the physician to review the images in order to prepare an examination report and/or diagnosis. In some embodiments, the physician terminal separately presents the clean set of images and the annotated set of images to the physician under different examination identification numbers.

The physician terminal may also present any photographs, audio recordings, or notes to the physician, which may take the place of an in-person meeting between the operator and the physician. In some embodiments, the physician terminal allows the physician to selectively insert operator notes into the physician's examination report After review by the physician, the server may automatically delete any content tagged as non-persistent. Deletion may take place in various ways. For example, the server may automatically delete any content tagged as non-persistent in response to review thereof by the physician or in response to generation or closing of an examination report by the physician. In other embodiments, the server periodically deletes the content tagged as non-persistent.

DETAILED DESCRIPTION

Figure 1:
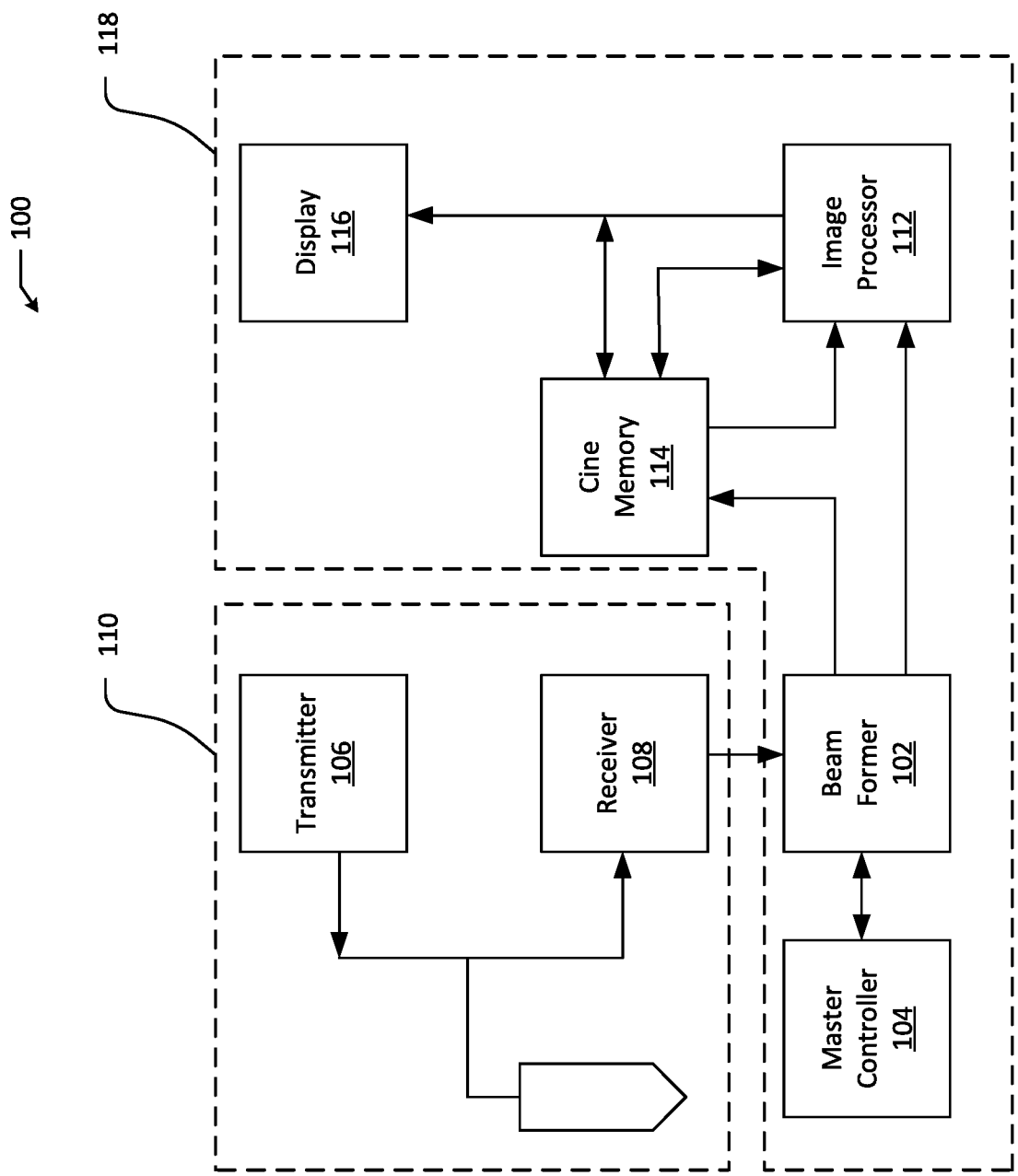
FIG. 1 is a schematic block diagram of an exemplary ultrasound imaging device.

Workflow efficiencies within a hospital environment continue to be an important area of focus due to the continued economic pressure of reducing overall health care costs. In the ultrasound field, there has been a substantial focus on making the workflow highly efficient for the sonographer, but, unfortunately, there has been little or no focus on taking a more holistic view of the entire workflow from the point at which the patient enters the exam room to the time the reviewing physician submits their diagnostic report.

Currently, knowledge about the patient being examined is conveyed to the physician is through images collected by the sonographer along with both measurements, calculations, and image physiology landmark annotations that are transferred to the reviewing physician using a standard image format, such as a Digital Imaging and Communications in Medicine (DICOM) format.

Unfortunately, when the scan is abnormal because the patient is suffering from a disease state, the DICOM information needs to be supplemented with additional information that is not capable of being conveyed through the DICOM format and requires the sonographer to leave the room where the patient was scanned, stand outside the reviewing physicians review room until they are ready to look at the images, and, then, as the physician us reviewing the images, provide the physician with verbal and or hand written information about their findings and notes they observed as they were scanning the patient. This manual process is extremely inefficient as well prone to losing information. In general, only the physician is allowed to make a diagnosis of the patient's condition, and the notes and findings of the sonographer should not be included in the overall medical record of the patient as they are not licensed to perform such diagnoses.

The following disclosure provides a means for the ultrasound imaging device to be able to generate both clean images of the patient's medical record, as well as images that are annotated with the sonographer's notes and findings for the benefit of the reviewing physician. The images that are annotated with the sonographer's notes and findings are automatically removed from the patient exam information when the reviewing physician closes out the exam from their DICOM review station, and only the clean images are retained as part of the patient's medical records.

In addition to providing access to the notes and findings of the sonographer on a set of annotated images, the system may enable the physician to either accept or reject the sonographer's notes and findings so that, when they are done reviewing the exam, at least part of the report for the patient's record can be automatically generated from the collection of the images and operator notes requiring little to no additional work of the physician along with alleviating the need for the sonographer to have a face-to-face meeting with the physician after every exam. This results in a substantial improvement in the workflow of the sonographer as well as that of the physician. The ability to ensure that all of the information gathered, including the notes and findings of the sonographer, is conveyed to the physician on the appropriate images increases workflow efficiency. Patient satisfaction is also increased as they are not abandoned in the exam room as the sonographer waits for the reviewing physician to become available.

Beyond being able to add additional information to the medical images that does not persist to the patient records, it is also beneficial for the sonographer to include pictures that they may have taken into the data being sent to the reviewing physician. These pictures could originate, for example, from the camera on a phone or tablet. The information contained in these pictures could also be drawings that the sonographer has made, including notes on the anatomy of the patient or other information that might be pertinent to the reviewing physician in making their diagnosis.

Given that the supplemental content supplied by the sonographer does not properly belong in the patient's medical record unless incorporated by the reviewing physician, it may be tagged for deletion by the system so as to not persist into the patients' medical records after the reviewing physician has made their diagnosis. The above-described workflow provides an additional pathway for the sonographer to supply the reviewing physician with as much information as possible so that they are able to make the best possible diagnosis for the patient in a timely and efficient manner.

Reference is now made to the figures, where like components are designated by like reference numerals throughout the disclosure. Some of the infrastructure that can be used with embodiments disclosed herein is already available, such as general-purpose computers, computer programming tools and techniques, digital storage media, and communications networks. A computing device may include a processor such as a microprocessor, microcontroller, logic circuitry, or the like. The processor may include a special purpose processing device such as an ASIC, PAL, PLA, PLD, FPGA, or other customized or programmable device.

The computing device may also include a computer-readable storage device such as non-volatile memory, static RAM, dynamic RAM, ROM, CD-ROM, disk, tape, magnetic, optical, flash memory, or other non-transitory computer-readable storage medium.

Various aspects of certain embodiments may be implemented using hardware, software, firmware, or a combination thereof. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc., which performs one or more tasks or implements particular abstract data types.

In certain embodiments, a particular software module may comprise disparate instructions stored in different locations of a computer-readable storage medium, which together implement the described functionality of the module. Indeed, a module may comprise a single instruction or many instructions, and may be distributed over several different code segments, among different programs, and across several computer-readable storage media. Some embodiments may be practiced in a distributed computing environment where tasks are performed by a remote processing device linked through a communications network.

The embodiments of the disclosure will be best understood by reference to the drawings. The components of the disclosed embodiments, as generally described and illustrated in the figures herein, could be arranged and designed in a wide variety of different configurations. Furthermore, the features, structures, and operations associated with one embodiment may be applicable to or combined with the features, structures, or operations described in conjunction with another embodiment. In other instances, well-known structures, materials, or operations are not shown or described in detail to avoid obscuring aspects of this disclosure.

Thus, the following detailed description of the embodiments of the systems and methods of the disclosure is not intended to limit the scope of the disclosure, as claimed, but is merely representative of possible embodiments. In addition, the steps of a method do not necessarily need to be executed in any specific order, or even sequentially, nor need the steps be executed only once.

FIG. 1 is a schematic block diagram of one exemplary embodiment of a medical imaging device, such as an ultrasound imaging device 100. Those skilled in the art will recognize that the principles disclosed herein may be applied to a variety of medical imaging devices, including, without limitation, an X-ray imaging device, a computed tomography (CT) imaging device, a magnetic resonance imaging (MRI) device, and a positron-emission tomography (PET) imaging device. As such, the components of each device may vary from what is illustrated in FIG. 1.

In one embodiment, the ultrasound imaging device 100 may include an array focusing unit, referred to herein as a beam former 102, by which image formation can be performed on a scanline-by-scanline basis. The device may be controlled by a master controller 104, implemented by a microprocessor or the like, which accepts operator inputs through an operator interface and in turn controls the various subsystems of the device 100.

For each scanline, a transmitter 106 generates a radio-frequency (RF) excitation voltage pulse waveform and applies it with appropriate timing across a transmit aperture (defined, in one embodiment, by a sub-array of active elements) to generate a focused acoustic beam along the scanline.

RF echoes received by receive aperture or receiver 108 are amplified, filtered, and then fed into the beam former 102, which may perform dynamic receive focusing, i.e., realignment of the RF signals that originate from the same locations along various scan lines. Collectively, the transmitter 106 and receiver 108 may be components of a transducer 110. Various types of transducers 110 are known in the ultrasound imaging art, such as linear probes, curvilinear probes, and phased array probes.

An image processor 112 may perform processing tasks specific to various active imaging mode(s) including 2D scan conversion that transforms the image data from an acoustic line grid into an X-Y pixel image for display. For other modes, such as a spectral Doppler mode, the image processor 112 may perform wall filtering followed by spectral analysis of Doppler-shifted signal samples using typically a sliding FFT-window. The image processor 112 may also generate a stereo audio signal output corresponding to forward and reverse flow signals. In cooperation with the master controller 104, the image processor 112 may also format images from two or more active imaging modes, including display annotation, graphics overlays and replay of cine loops and recorded timeline data.

A cine memory 114 provides resident digital image storage to enable single image or multiple image loop review, and acts as a buffer for transfer of images to digital archival devices, such as hard disk drives or optical storage. In some systems, the video images at the end of the data processing path may be stored to the cine memory. In state-of-the-art systems, amplitude-detected, beamformed data may also be stored in cine memory 114. For spectral Doppler mode, wall-filtered, baseband Doppler I/Q data for a user-selected range gate may be stored in cine memory 114. Subsequently, a display 116, such as a computer monitor, may display ultrasound images created by the image processor 112 and/or images using data stored in the cine memory 114.

The beam former 102, the master controller 104, the image processor 112, the cine memory 114, and the display 116 can be included as part of a main processing console 118 of the ultrasound imaging device 100, which may include more or fewer components or subsystems than are illustrated. The ultrasound transducer 110 may be incorporated into an apparatus that is separate from the main processing console 118, e.g. in a separate apparatus that is wired or wirelessly connected to the main processing console 118. This allows for easier manipulation of the ultrasound transducer 110 when performing specific ultrasound procedures on a patient. Further, the transducer 110 can be an array transducer that includes an array of transmitting and receiving elements for transmitting and receiving ultrasound waves.

Those skilled in the art recognize that a wide variety of ultrasound imaging devices are available on the market, and additional details relating to how images are generated is unnecessary for a thorough understanding of the principles disclosed herein.

Figure 2:
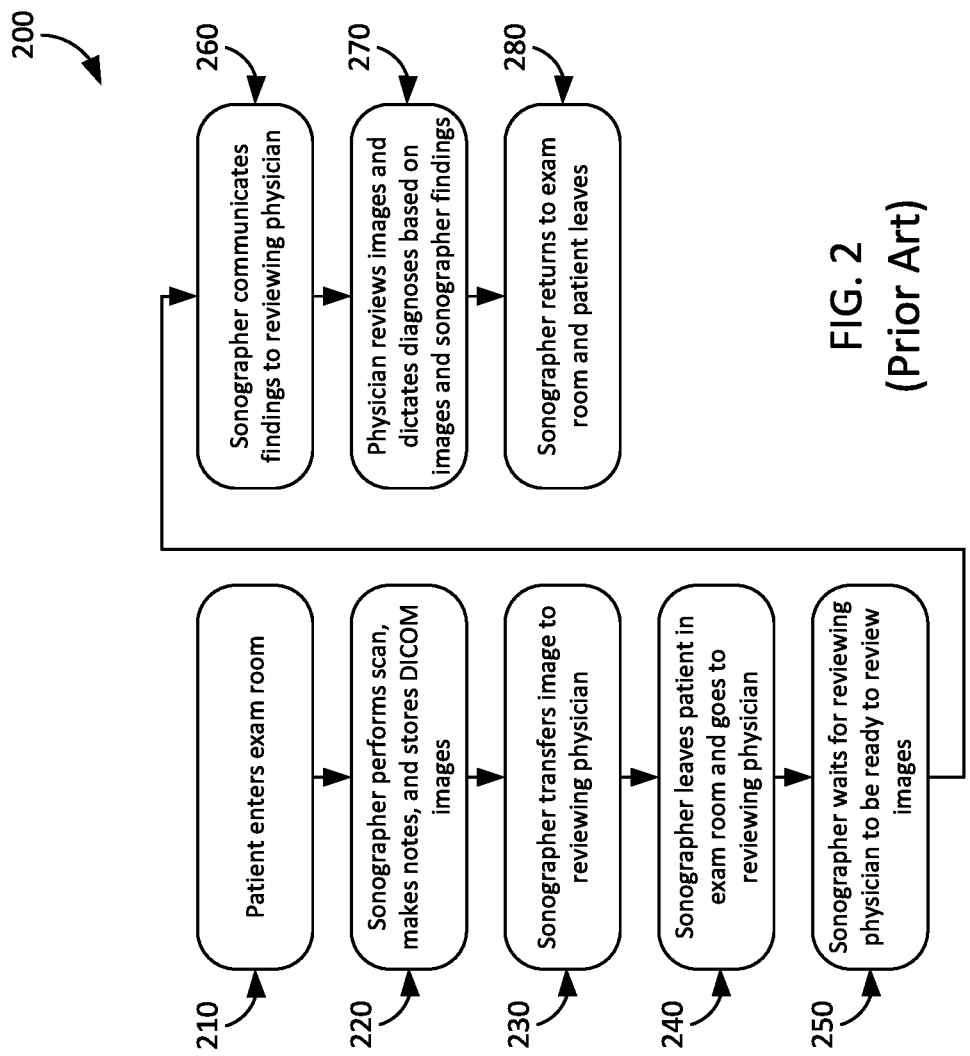
FIG. 2 is a flowchart of a current ultrasound imaging workflow.

FIG. 2 is a flow diagram of a conventional hospital workflow 200. While the workflow 200 is described in the context of ultrasound imaging, a similar workflow may be used with other imaging devices. The workflow 200 begins when the patient enters the room at step 210. Thereafter, the patient is scanned by the sonographer at step 220. As the sonographer is scanning, they make either mental notes or written notes while gathering the necessary images for the requested scan for the reviewing physician.

Once the basic exam by the sonographer is completed, the sonographer, at step 230, closes the exam on the ultrasound imaging device and the images are transferred to a DICOM server (not shown) so that the reviewing physician can read the images. At step 240, the sonographer typically leaves the exam room and goes to a physician reviewing room. At step 250, the sonographer typically waits outside the physician review room until the reviewing physician is available to read the images, which can take anywhere from a few minutes to over a half hour.

At step 260, when the reviewing physician is ready to look at the images, the sonographer will enter the reviewing room and stand behind the physician, verbally communicating their observations and thoughts about the exam. Thereafter, the reviewing physician continues to review the images and then enters or dictates their diagnosis at step 260. The sonographer then returns to the patient room at step 280, after which the patient leaves the room, often an hour or more after arriving for the exam.

Figure 3:
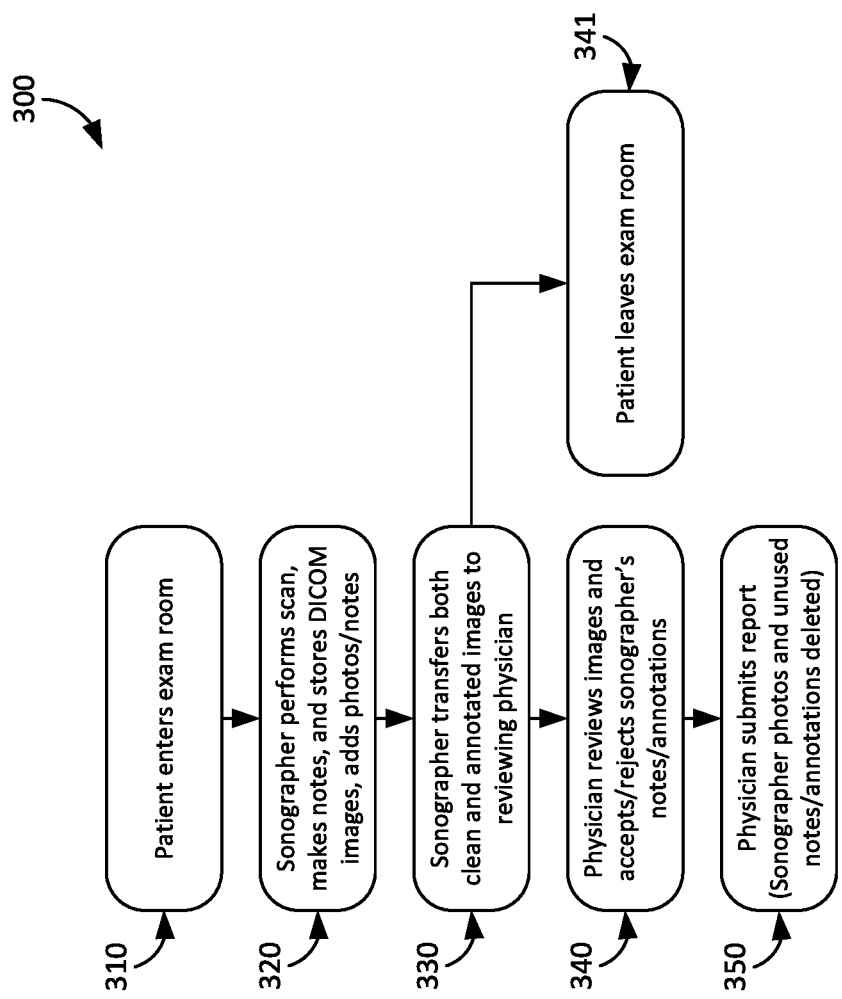
FIG. 3 is a flowchart of an improved ultrasound imaging workflow according to one embodiment.

FIG. 3 is a flow diagram of a hospital workflow 300 according to one embodiment. The modified workflow 300 starts with the patient entering the room at step 310. Once the patient is in the room, at step 320, the sonographer performs the ultrasound exam, making all of the standard measurements, calculations, and anatomic annotations that they would perform on a traditional set of ultrasound exam images. However, in addition, the sonographer is able to tag as "non-persistent" various additional information, observations, findings, photos of drawings, or the like, which are included in or with the examination image set, but will be treated as non-persistent in the final exam of record.

At step 330, once the sonographer is done with the basic exam, they will transfer both the clean and annotated images to the reviewing physician via the DICOM format to the reviewing physician. In one embodiment, a set of images and supplemental content may be tagged as non-persistent and transferred via the DICOM format or another modality to the reviewing physician.

At this time, all the traditional data that the sonographer would have communicate orally has been provided to the physician, so there is no need for the sonographer to leave the exam room. Accordingly, at step 341, the patient can leave the exam room and the next patient can enter. As described more fully below, at step 350, the reviewing physician may accept the opinions and/or findings of the sonographer, which will populate the report along with any of the standard measurements, calculations, and/or anatomical identifications/descriptions. If the physician disagrees with the opinions of the sonographer, he or she can reject them and generate a report with a different diagnosis. In either case, any photographs, notes, or annotations tagged as non-persistent will be automatically deleted, and only the clean images and physician's report will be entered into the patient's medical record.

Figure 4:
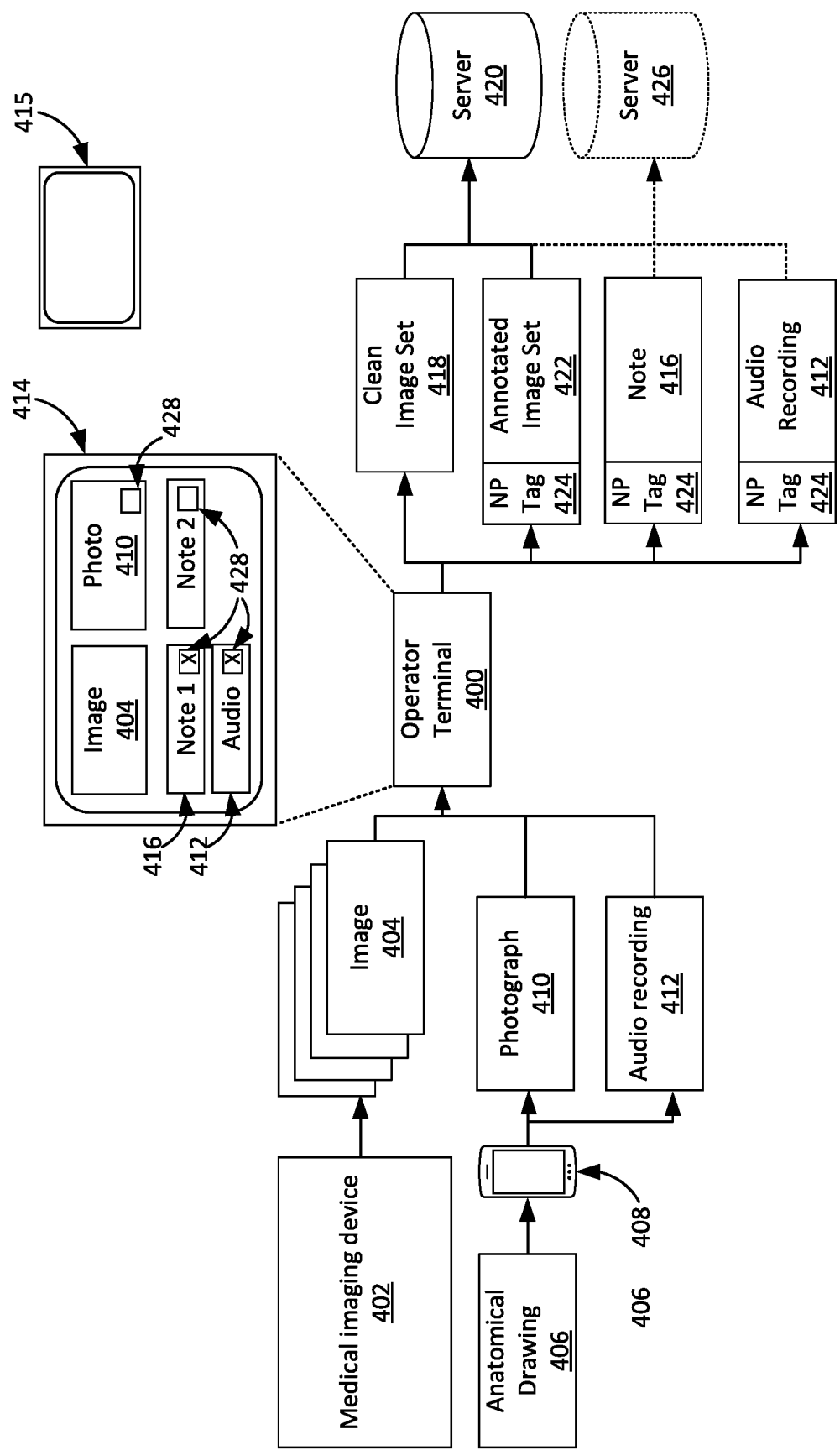
FIG. 4 illustrates the flow of data through an operator terminal.

FIG. 4 illustrates the flow of data through an operator terminal 400. As noted above, the medical imaging device 402 may include, but is not limited to, an ultrasound imaging device. An operator uses the medical imaging device 402 to scan the patient and generate a set of diagnostic images 404 as specified by a workflow for a particular type of examination ordered by a physician. The images 404 may be generated a variety of formats, including the DICOM format, which is extensively used in the medical field to enable interoperability between devices and systems. The DICOM format allows an image or series of images to be stored in an object along with various identifiers and other data.

In some cases, the operator may also prepare one or more anatomical drawings 406 during the course of an exam, which may be prepared by hand or with the assistance of a portable device 408. The anatomical drawing 406 may depict, for example, a structure observed by the operator that may not have been perfectly represented in the images 404, e.g., a tumor or other abnormality.

In one embodiment, the operator uses the portable device 408, which could be a cellular phone, a tablet with a camera, or any other imaging modality apart from the medical imaging device 402, to take a photograph 410 of the anatomical drawing 408. Alternatively, or in addition, the operator may use the portable device 408, or another device, such as a microphone (not shown), to generate an audio recording 412. The audio recording 412 may include a verbal description by the operator of their findings or observations pertaining to the images 404.

The images 404, photographs 410, and audio recordings 412 may be supplied to the operator terminal 400, which may be displayed/presented on the same display device 414, and/or a separate display device 415, and/or the operator's mobile device 408. The operator terminal 400, including the display device(s) 414, 415, may be components of the medical imaging device 402 or a standalone computer terminal in communication with the medical imaging device 402.

The operator terminal 400 may enable the operator of the medical imaging device 402 to enter one or more notes 416, which may include various findings or observations of the operator. In one embodiment, the notes 416 may exclude measurements, calculations, or descriptions of anatomical locations normally associated with diagnostic images 404 generated by a medical imaging device 402. As such, the notes 416 may include content that would typically be inappropriate to include in a patient's chart or permanent medical records (unless explicitly approved or incorporated by a physician), such as preliminary diagnoses for which the operator is not licensed to make. The notes may be associated with or annotate specific images 404 or portions thereof in order to bring the physician's attention to particular abnormalities. In other embodiments, some notes may not be specifically stored with or used to annotate an image, but may be stored separately for review by a physician.

In one embodiment, the operator terminal 400 outputs a set of clean images 418 to a server 420, such as a DICOM server. The clean images 418 may be identical to the set of diagnostic images 404 output by the medical imaging device 402. Alternatively, the clean images 418 may be similar to the set of images 404 but formatted in a specific format, such as the DICOM format. In other cases, the clean images 418 may additionally include standard measurements, calculations, or descriptions of anatomical locations entered by the operator.

In addition, the operator terminal 400 outputs a set of annotated images 422. The annotated images 422 may be generated through a process of annotating the original diagnostic images 404 with the associated notes 416, photographs 410 and audio recordings 412 provided by the operator, collectively referred to herein as supplemental content. The supplemental content may be included, for example, in a DICOM object using one or more custom tags. Alternatively, or in addition, some of the supplemental content may be overlaid upon the original images 404, such as that the annotated images 422 appear marked up with the supplemental content. In still other embodiments, some of the supplemental content may be stored in the server 420 using a separate file or file format, i.e., not part of the annotated images 422.

In one embodiment, the operator terminal 400 tags the annotated images 422 and/or any other supplemental content as "non-persistent," i.e., the tagged annotated images 422 and/or other supplemental content should not persist to the physician's report and/or patient chart/record (unless explicitly incorporated by the physician). Data may be tagged or designated as non-persistent may means of a non-persistent tag 424, which may include any suitable data structure. The non-persistent tag 424 may be implemented using a custom DICOM tag, a database entry, a watermark, or other similar mechanism.

In other embodiments, the annotated images and/or various supplemental content may not be stored in the same server 420 as the clean images 418. Rather, a supplemental content server 426 may be used for this purpose. Therefore, as used herein, the term "server" may refer to one server or multiple servers including one or more storage devices. Likewise, the clean images 418, the annotated images 422, the notes 416, and the audio recordings 412 may be stored in the same format or a different format, in one file or multiple files, in a single DICOM object or multiple objects, or in one server or multiple servers of the same or different type.

In one embodiment, the operator terminal 400 provides a visual tagging mechanism 428, such as a check box or other user interface mechanism, to selectively designate certain supplemental content as non-persistent. Items designated on the display device 412 using the tagging mechanism 428 may be affirmatively associated with a non-persistent tag 424. In other embodiments, all operator-provided information, other than standard measurements, calculations, or identifications of anatomical locations, will be automatically tagged with a non-persistent tag, in which case the operator may be enabled to de-select, in certain embodiments, various content using the tagging mechanism 428.

Figure 5:
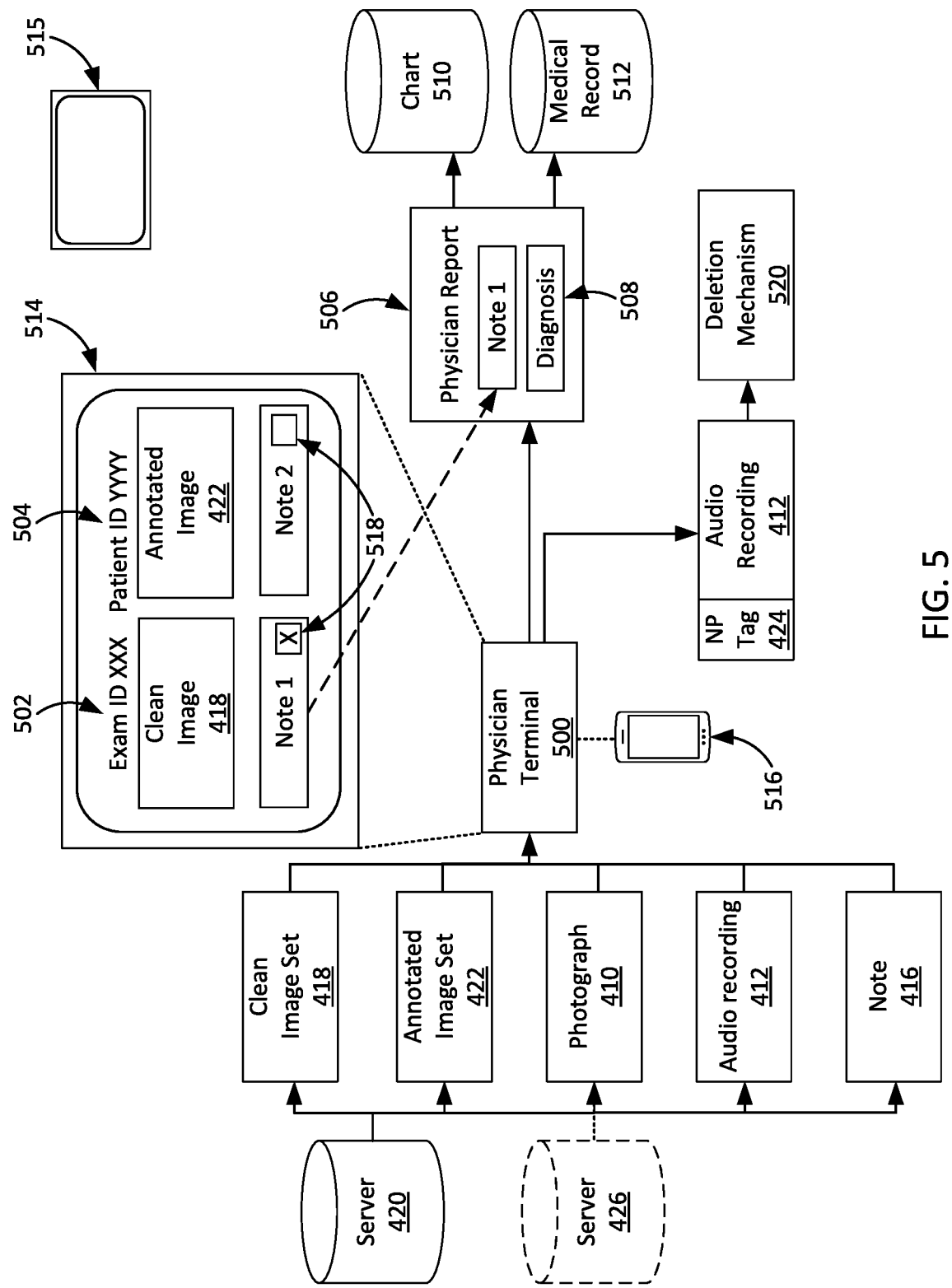
FIG. 5 illustrates the flow of data through a physician terminal.

FIG. 5 illustrates the flow of data through a physician terminal 500. In one embodiment, the clean image set 418 and annotated image set 422, as well as any photographs 410, audio recordings 412, or notes 416 (i.e., supplemental content) are retrieved from the server 420 and/or supplemental content server 426. Retrieval may be accomplished, for example, based on an exam ID 502 and/or patient ID 504.

One purpose of the physician terminal 500 is to allow the physician to review the image(s) 418, 422, as well as any supplemental content 410, 412, 416. Another purpose of the physician terminal 500 is to allow the physician to prepare a physician's report 506, which will typically include at least one diagnosis 508. The report 506 may become part of the patient's chart 510 (in the case of a hospital visit) and/or permanent medical record 512. The chart 510 and medical record 512 may be combined in various embodiments and stored in one or multiple devices, including the server(s) 420, 426 or other suitable device(s).

In one embodiment, the physician terminal 500 may display one or more of the clean images 418 and/or annotated images 422 on the same display screen 514 or a separate display screen 515 (or mobile device 516) within a single viewing session based on the exam ID 502 and/or patient ID 504. Alternatively, the clean images 418 and annotated images 422 may be displayed in different sessions (not shown) with separate exam IDs in 502 in order to clearly distinguish the two. In either case, the clean images 418 and annotated images 422 will typically be associated with a patient ID 504 in order to properly identify the patient to whom the images 418, 422 belong.

The photographs 410, audio recordings 412, and notes 416 may be similarly presented to the physician for review. Such supplemental content may take the place of an in-person meeting between the physician and the operator. The photographs 410 and notes 416 may be displayed via the physician terminal 500 on the same display device 514 and/or the separate display device 515 and/or the mobile device 516. The audio recordings 412 may be audibly presented to the physician using a speaker (not shown) in one or more of the display device(s) 514, 515 and/or mobile device 516.

As noted above in connection with FIG. 4, the operator may have entered one or more notes 416 in connection with one or more of the images 418, 422, photographs 410, and/or audio recordings 412. The notes 416 may include the findings and/or observations of the operator, some of which may be relevant to the physician's report 506 and diagnosis 508. However, in most states, only a licensed physician may diagnose an illness. Therefore, such notes 416 of the operator would not normally be included in the patient's chart 510 and/or medical record 512.

In one embodiment, the physician terminal 500 provides a selection mechanism 518, such as a check box or the like, which allows the physician to select one or more of the operator's notes 416 to include in the physician's report 506. A similar or different selection mechanism 518 may also allow the physician to selectively include one or more of the clean images 418, annotated images 422, and/or photographs 410 in the physician's report 506. A similar or different selection mechanism 518 may also allow the physician to selectively include one or more of the clean images 418, annotated images 422, and/or photographs 410 in the patient's chart 510 and/or medical record 512 in certain instances, bypassing any non-persistent tags automatically or selectively added by the operator terminal 400 of FIG. 4.

In one embodiment, the images 418, 422, photographs 410, audio recordings 412, and/or notes 416 tagged with a non-persistent tag 424 may be automatically deleted by a deletion mechanism 520. The deletion mechanism 520 may be a hardware or software component of the servers 420, 426 and/or the physician terminal 500, which deletes content tagged as non-persistent therefrom.

In one embodiment, the deletion mechanism 520 may periodically delete any images 418, 422, photographs 410, audio recordings 412, and/or notes 416 associated with a non-persistent tag 424. For example, the deletion mechanism 520 may be configured to delete content tagged as non-persistent at regular intervals, such as hourly, daily, weekly, etc.

Alternatively, or in addition, the deletion mechanism 520 may delete content tagged as non-persistent in response to review thereof by the physician or generation or closing (including transmission) of the examination report 506 by the physician. In one embodiment, the deletion mechanism 520 prevents any content tagged as non-persistent from being included in the chart 510 and/or 512, unless explicitly provided otherwise by the physician.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

Those having skill in the art will appreciate that many changes may be made to the details of the above-described embodiments without departing from the underlying principles of the invention. The scope of the present invention should, therefore, be determined only by the following claims.

What is claimed is:

1. A computer-implemented method for automatically generating at least a portion of a physician report, the method comprising:

obtaining, at an operator terminal, at least one image of a patient generated by a medical imaging device in electronic communication with the operator terminal, wherein the medical imaging device comprises at least one of an ultrasound imaging device, an X-ray imaging device, a computed tomography (CT) imaging device, a magnetic resonance imaging (MRI) device, and a positron-emission tomography (PET) imaging device;

receiving, at the operator terminal, one or more notes pertaining to the at least one image from an operator of the medical imaging device, the one or more notes comprising supplemental content excluding measurements, calculations, or descriptions of anatomical locations, the one or more notes comprising at least one drawing or audio recording;

storing, in at least one Digital Imaging and Communications in Medicine (DICOM) server in one or more DICOM objects, a clean set of images including the at least one image, the clean set of images lacking the supplemental content;

automatically annotating, at the operator terminal, the at least one image with the one or more notes to generate an annotated set of images, wherein annotating comprises electronically overlaying the supplemental content upon the at least one image;

automatically tagging, at the operator terminal, all operator-provided supplemental content and each image in the annotated set of images containing operator-provided supplemental content as non-persistent by electronically associating the operator-provided supplemental content and each image in the annotated set of images containing operator-provided content with a custom DICOM tag;

storing, in the at least one DICOM server in one or more DICOM objects, the annotated set of images in association with the clean set of images for the patient;

automatically displaying to a physician, on a physician terminal separate from the operator terminal, both the clean set of images and the annotated set of images of the patient stored in the at least one DICOM server, wherein automatically displaying comprises electronically displaying a selection mechanism that allows the physician to selectively identify, via a single action, one or more of a particular image from the annotated set of images or particular operator-provided supplemental content to include in the physician report and, in response to a selection by the physician, disassociating the custom DICOM tag from the particular image or the particular operator-provided supplemental content;

automatically and electronically generating at least a portion of the physician report comprising the at least one particular image from the annotated set of images or the particular operator-provided supplemental content;

storing the physician report in at least one of a chart or permanent medical record of the patient; and automatically and electronically deleting, from the at least one DICOM server, all operator-provided supplemental content and each image of the annotated set of images tagged as non-persistent that have not been incorporated into the physician report.

2. A medical imaging system for automatically generating at least a portion of a physician report, comprising:

an operator terminal configured to:

obtain at least one image of a patient generated by a medical imaging device in electronic communication with the operator terminal, wherein the medical imaging device comprises at least one of an ultrasound imaging device, an X-ray imaging device, a computed tomography (CT) imaging device, a magnetic resonance imaging (MRI) device, and a positron-emission tomography (PET) imaging device;

receive one or more notes pertaining to the at least one image from an operator of the medical imaging device, the one or more notes comprising supplemental content excluding measurements, calculations, or descriptions of anatomical locations, the one or more notes comprising at least one drawing or audio recording;

store a clean set of images including the at least one image in at least one Digital Imaging and Communications in Medicine (DICOM) server in one or more DICOM objects, the clean set of images lacking the supplemental content;

automatically annotate the at least one image with the one or more notes to generate an annotated set of images by associating the at least one image with a custom DICOM object including the one or more notes or electronically overlaying the supplemental content upon the at least one image;

automatically tag all operator-provided supplemental content and each image in the annotated set of images containing operator-provided supplemental content as non-persistent by electronically associating the operator-provided supplemental content and each image in the annotated set of images containing operator-provided content with a custom DICOM tag; and store the annotated set of images in the at least one DICOM server with the clean set of images for the patient in association with the clean set of images for the patient;

wherein the at least one DICOM server is configured to:

automatically display to a physician on a physician terminal separate from the operator terminal, both the clean set of images and the annotated set of images stored for the patient;

automatically display a selection mechanism that allows the physician to selectively identify, via a single action, one or more of a particular image from the annotated set of images or particular operator-provided supplemental content to include in the physician report and, in response to a selection by the physician, disassociate the custom DICOM tag from the particular image or the particular operator-provided supplemental content;

automatically and electronically generate at least a portion of the physician report comprising the at least one particular image from the annotated set of images or the particular operator-provided supplemental content;

storing the physician report in at least one of a chart or permanent medical record of the patient; and automatically and electronically delete from the at least one DICOM server all operator-provided supplemental content and each image of the annotated set of images tagged as non-persistent that have not been incorporated into the physician report.

3. The medical imaging system of claim 2, wherein the physician terminal is configured to include one or more images from the clean set of images in a medical record or chart of the patient without including any of the supplemental content or images tagged as non-persistent.

4. The medical imaging system of claim 2, wherein the at least one DICOM server is configured to automatically delete any supplemental content or images tagged as non-persistent and not explicitly approved or incorporated into a permanent medical record in response to review thereof by the physician.

5. The medical imaging system of claim 2, wherein the at least one DICOM server is configured to automatically delete any supplemental content or images tagged as non-persistent and not explicitly approved or incorporated into a permanent medical record in response generation or closing of an examination report by the physician.

6. The medical imaging system of claim 2, wherein the at least one DICOM server is configured to periodically delete any supplemental content or images tagged as non-persistent and not explicitly approved or incorporated into a permanent medical record by the physician.

7. The medical imaging system of claim 2, wherein the physician terminal is further configured to allow the physician to selectively insert one or more notes from the operator into an examination report.

8. The medical imaging system of claim 2, wherein the operator terminal is configured to tag an operator-selected annotated image as non-persistent.

9. The medical imaging system of claim 2, wherein the physician terminal is configured to separately present the clean set of images and the annotated set of images to the physician under different examination identification numbers.

10. The medical imaging system of claim 2, wherein the operator terminal is further configured to receive one or more photographs related to the patient from the operator of the medical imaging device, tag the one or more photographs as non-persistent, and store the one or more photographs in the at least one DICOM server, wherein the one or more photographs are generated by a secondary imaging modality other than the medical imaging device;
 wherein the physician terminal is further configured to present the one or more photographs to the physician with the clean set of images and the annotated set of images of the patient; and
 wherein the at least one DICOM server is further configured to automatically delete the one or more photographs tagged as non-persistent after review thereof by the physician.

11. The medical imaging system of claim 10, wherein the at least one DICOM server is configured to automatically delete the one or more photographs tagged as non-persistent in response to review thereof by the physician or generation or closing of an examination report by the physician.

12. The medical imaging system of claim 2, wherein the operator terminal is further configured to receive one or more audio recordings of the operator of the medical imaging device pertaining to the at least one image, tag the one or more audio recordings as non-persistent, and store the one or more audio recordings in the at least one DICOM server;
 wherein the physician terminal is further configured to present the one or more audio recordings to the physician with the clean set of images and the annotated set of images of the patient; and
 wherein the at least one DICOM server is further configured to automatically delete the one or more audio recordings tagged as non-persistent after review thereof by the physician.

13. The medical imaging system of claim 2, wherein the operator terminal is further configured to receive one or more additional notes from the operator of the medical imaging device pertaining to the at least one image, tag the one or more additional notes as non-persistent, and store the one or more additional notes in the at least one DICOM server;
 wherein the physician terminal is further configured to present the one or more additional notes to the physician with the clean set of images and the annotated set of images of the patient; and
 wherein the at least one DICOM server is further configured to automatically delete the one or more additional notes tagged as non-persistent from the at least one DICOM server after review thereof by the physician.

14. The medical imaging system of claim 13, wherein the at least one DICOM server is configured to automatically delete the one or more additional notes tagged as non-persistent in response to review thereof by the physician or generation or closing of an examination report by the physician.

15. The medical imaging system of claim 13, wherein the physician terminal is further configured to allow the physician to selectively insert the one or more additional notes into an examination report prepared by the physician.

16. At least one non-transitory computer-readable medium comprising program code that, when executed by at least one processor, cause the at least one processor to perform a method for automatically generating at least a portion of a physician report, the method comprising:
 obtaining, at an operator terminal, at least one image of a patient generated by a medical imaging device in electronic communication with the operator terminal, wherein the medical imaging device comprises at least one of an ultrasound imaging device, an X-ray imaging device, a computed tomography (CT) imaging device, a magnetic resonance imaging (MRI) device, and a positron-emission tomography (PET) imaging device;
 receiving, at the operator terminal, one or more notes pertaining to the at least one image from an operator of the medical imaging device, the one or more notes comprising supplemental content excluding measurements, calculations, or descriptions of anatomical locations, the one or more notes comprising at least one drawing or audio recording;
 storing, in at least one Digital Imaging and Communications in Medicine (DICOM) server in one or more DICOM objects, a clean set of images including the at least one image, the clean set of images lacking the supplemental content;
 automatically annotating, at the operator terminal, the at least one image with the one or more notes to generate an annotated set of images, wherein annotating comprises electronically overlaying the supplemental content upon the at least one image;
 automatically tagging, at the operator terminal, all operator-provided supplemental content and each image in the annotated set of images containing operator-provided supplemental content as non-persistent by electronically associating the operator-provided supplemental content and each image in the annotated set of images containing operator-provided content with a custom DICOM tag;
 storing, in the at least one DICOM server, the annotated set of images in association with the clean set of images for the patient;
 automatically displaying to a physician, on a physician terminal separate from the operator terminal, both the clean set of images and the annotated set of images of the patient stored in the at least one DICOM server, wherein automatically displaying comprises electronically displaying a selection mechanism that allows the physician to selectively identify, via a single action, one or more of a particular image from the annotated set of images or particular operator-provided supplemental content to include in the physician report;
 automatically and electronically generating at least a portion of the physician report comprising the at least one particular image from the annotated set of images or the particular operator-provided supplemental content;
 storing the physician report in at least one of a chart or permanent medical record of the patient; and
 automatically and electronically deleting, from the at least one DICOM server, all operator-provided supplemental content and each image of the annotated set of images tagged as non-persistent that have not been incorporated into the physician report.

* * * * *